(12) United States Patent
Provost et al.

(10) Patent No.: US 11,413,364 B1
(45) Date of Patent: Aug. 16, 2022

(54) TOP LOAD DISINFECTION DEVICE FOR DISINFECTING A CONTAINER

(71) Applicant: Steribin, LLC, St. George, UT (US)

(72) Inventors: Wayne A. Provost, St. George, UT (US); Jonathan M. Cole, St. George, UT (US); Jeffrey Stewart, St. George, UT (US)

(73) Assignee: Steribin, LLC, St. George, UT (US)

( * ) Notice: Subject to any disclaimer, the term of this patent is extended or adjusted under 35 U.S.C. 154(b) by 0 days.

(21) Appl. No.: 17/315,214

(22) Filed: May 7, 2021

(51) Int. Cl.
| | |
|---|---|
| *A61L 2/00* | (2006.01) |
| *G01N 21/00* | (2006.01) |
| *G01N 23/00* | (2006.01) |
| *A61N 5/00* | (2006.01) |
| *A61L 2/10* | (2006.01) |
| *B65G 15/00* | (2006.01) |

(52) U.S. Cl.
CPC ............... *A61L 2/10* (2013.01); *B65G 15/00* (2013.01); *A61L 2202/11* (2013.01); *A61L 2202/14* (2013.01); *A61L 2202/23* (2013.01); *B65G 2201/0235* (2013.01)

(58) Field of Classification Search
CPC ................ A61L 2/00; A61L 2/10; A61L 2/24
USPC ............ 422/24; 250/453.11, 454.11, 455.11, 250/492.1
See application file for complete search history.

(56) References Cited

U.S. PATENT DOCUMENTS

| | | | |
|---|---|---|---|
| 6,702,985 B1 * | 3/2004 | Taggart ................. | B67C 7/0073 422/302 |
| 2009/0252646 A1 * | 10/2009 | Holden ................... | A63F 11/00 422/186.3 |
| 2016/0101201 A1 * | 4/2016 | Franc ...................... | B67B 3/003 422/24 |

* cited by examiner

*Primary Examiner* — Monzer R Chorbaji
(74) *Attorney, Agent, or Firm* — Gurr Brande & Spendlove, PLLC; Robert A. Gurr

(57) ABSTRACT

A top load device for disinfecting a container, such as a security bin for use in an airport, the device configured to store a stack of contaminated containers, wherein the device separates and releases a single container into an interior of a housing for disinfection. The housing comprises a conveyor that moves the container through the interior of the housing from an initial location to an exit of the housing, wherein the container is disinfected or sanitized with electromagnetic wavelength as it moves through the interior of the housing.

15 Claims, 13 Drawing Sheets

TOP LOAD DISINFECTION DEVICE FOR DISINFECTING A CONTAINER

FIELD OF THE INVENTION

The present invention relates generally to a device, (herein referred to as a "disinfecting device"), systems, and methods for treating a contaminated container.

BACKGROUND OF THE INVENTION

Infectious diseases commonly spread through the direct transfer of bacteria, viruses or other microbes from contact with contaminated surfaces. Surfaces which are generally understood as having a high likelihood of contamination (i.e., toilets, cutting boards, hands, etc.) or which require high levels of sterility (i.e, surgical instruments, food, etc.) are frequently treated to reduce contamination. These treatments may be as simple as handwashing, or as complex as gamma irradiation. In some instances, a surface may be understood as having a high likelihood of contamination, but the treatment of the surface may be complicated or untreatable due to the material or functional properties of the surface. In some instances, the likelihood of contamination of a surface may be unknown or underappreciated such that the surface is not treated.

For example, more than 2.8 billion people travel by commercial aircraft each year. Travelers often have concerns about the health risks of air travel, including in-flight medical emergencies, exacerbations of chronic medical problems due to changes in air pressure and humidity, barotrauma, relative immobility during flights, close proximity to other passengers with certain communicable diseases, and potential adverse effects of prolonged exposure to recirculated air. In addition to these risks is the underappreciated risk of microbial exposure prior to boarding the plane, namely through contact with contaminated surfaces in the airport.

Bacterial culture tests performed on a variety of airport surfaces revealed high levels of bacteria and viruses on security bins, arm rests, seatbelt buckles, and tray tables. While it is possible to use sanitizer wipes and/or sprays to disinfect arm rests, seatbelt buckles, and tray tables, over time these methods of disinfection produce sticky residues that are not compatible for use with stackable security bins. Accordingly, although methods for disinfecting contaminated airport surfaces exists, challenges still remain. The present invention addresses and overcomes these challenges.

BRIEF SUMMARY OF THE INVENTION

The present invention relates generally to a device for disinfecting a container, such as a security bin for use in an airport. In particular, the present invention relates to a top load disinfecting device having an opening configured to store a stack of contaminated containers, wherein the device releases a single container into an interior of a housing for disinfection. The housing comprises a conveyor that moves the container through the interior of the housing from an initial location to an exit of the housing, wherein the container is disinfected or sanitized with an antimicrobial electromagnetic wavelength as it moves through the interior of the housing. As used herein, the terms "light" and "electromagnetic wavelength" are understood to describe any wavelength of light capable of destroying or inhibiting the growth of microorganisms, especially pathogenic microorganisms. Once the container is disinfected or sanitized, a distal end of the container extends beyond the exit of the housing such that a user may remove the container entirely from the housing. In some instances, the housing comprises a sensor in proximity to the exit and configured to detect the presence of a container within the exit of the housing, such that when a container is removed from the exit of the housing, a new contaminated container is released from the opening and into the interior of the housing. In some instances, the sensor in proximity to the exit may be overridden to permit continuous feeding of contaminated containers into the housing.

In some instances, the opening comprises a sensor configured to detect the presence of two or more contaminated containers within the opening, such that when two or more contaminated containers are detected within the opening, a single contaminated container may be released into the housing, and such that when two or more contaminated containers are not detected within the opening, a single contaminated container is not released into the housing, but rather remains in the opening to prevent leakage of light (i.e., electromagnetic wavelengths emitted from the light source) through the opening. In some instances, the opening and the exit may comprise profiled shapes that mirror a profile of a contaminated container.

In some instances, the housing may comprise one or more light seals configured to prevent leakage of light (i.e., electromagnetic wavelengths emitted from the light source) through the opening and/or the exit of the housing. In some instances, the opening and the exit of the housing may comprise light seals configured to close a gap between the respective opening and a surface of the contaminated container. In some instances, a light seal may be positioned to prevent binding between the container and the light seal. For example, the light seal may be angled towards the exit of the housing. In some instances, a light seal may be positioned to match a profile or shape of the container. For example, the light seal may comprise a cutout that mirrors a profile or shape of the container, or the light seal may be secured to the opening and/or the exit to replicate the shapes thereof.

The present invention further includes a method for disinfecting a container, wherein the method utilize a top load disinfecting device disclosed herein.

In some instances, a top load disinfecting device is provided which is configured to disinfect, sanitize, or otherwise treat and lessen a contaminated condition of one or more surfaces of a container. As used herein, the term "container" is understood to include any object that can be used to hold or transport something. Although the features of the present invention are generally discussed in connection with a security bin container, each feature of each embodiment disclosed herein may be implemented with any container, as defined herein. Further, although generally referred to herein as a "disinfecting device", it is understood that a disinfecting device of the present invention may disinfect, sterilize, sanitize, or otherwise treat and clean one or more surfaces of a contaminated container to achieve a lessened state or condition of contamination. In some instances, a disinfecting device is configured to treat a container to achieve a sterilized condition. In some instances, a disinfecting device is configured to treat a container to achieve a sanitized condition. In some instances, a disinfecting device is configured to treat a container to achieve a disinfected condition.

In a first set of example embodiments, the top load disinfecting device may include a housing having an opening for receiving a stack of contaminated containers, the housing further comprising an interior into which a single contaminate container is released. The housing includes a set of drop plates arranged in proximity to the opening and configured to support the stack of contaminated containers. In some instances, the set of drop plates comprises four drop plates arranged in proximity to the corners of the contaminated containers. The drop plates have upper and lower portions for supporting the contaminated containers. The drop plates further comprise a ramped surface configured for insertion between adjacent contaminated containers, wherein the ramped surface separates and releases a lower contaminated container from an adjacent upper contaminated container. Once released, the lower contaminated container falls through the opening of the housing an into the interior of the housing, while the remaining contaminated container are supported by the set of drop plates.

Each drop plate is coupled to and supported by a vertical axle configured to rotate each respective drop plate about a central vertical axis of the drop plate. The rotation of the set of drop plates is coordinated and synchronized such that contact between each drop plate and the contaminated containers is identical at the location of each drop plate. The vertical axles are coupled to a motor that drives the rotation of the axles and their respective drop plates. In some instances, the motor is coupled to the vertical axles via a plurality of pulleys and one or more belt drives. In some instances, each vertical axis is directly driven by a separate motor. In some instances, the direction of rotation of the drop plates is identical (i.e., collectively clockwise and/or counterclockwise). In some instances, the direction of rotation of the drop plates is mixed, such that a drop plate rotates in a first direction while a second drop plate rotates in a second direction that is opposite the first direction.

In some instances, the drop plates rotate about a vertical axis to achieve various positions for the purposes of storing, separating and releasing contaminated containers into the top load disinfecting device. In some instances, the drop plates alternate clockwise and counterclockwise rotations (between 120° and 270°) to achieve the various positions. In some instances, the drop plates rotate 360° in a single direction to achieve the various positions. In some instances, the drop plates comprise a storage position by which a stack of contaminated containers is supported on a lower portion of each drop plate. In some instances, the drop plates comprise a transfer position by which an upper contaminated container is supported on an upper portion of each drop plate and a lower contaminated container is unsupported by a lower portion of each drop plate. In some instances, the drop plates comprise a biasing position by which a ramped surface of each drop plate is wedged between an upper contaminated container and a lower contaminated container to bias the lower contaminated container away from the upper contaminated container. In some instances, the drop plates comprise a release position by which a ramped surface of each drop plate is fully wedged between an upper contaminated container and a lower contaminated container such that a vacuum between the lower contaminated container and the upper contaminated container is broken and the lower contaminated container is released from the upper contaminated container. Following the release position, in some instances the drop plates are further rotated to the storage position, whereby the stack of contaminated containers is transferred from the upper portion to the lower portion of the drop plate.

In some instances, the lower and upper portions are separate components having fixed positions relative to one another. In some instances, the positions of the lower and upper portions are fixed by the vertical axles. For example, the lower and upper portions may comprise keyed central openings that engage a keyed surface of the vertical axle. In some embodiments, the upper and lower portions are monolithically formed as a single structure.

In some instances, the housing comprises a conveyor configured to move a contaminated container through the interior of the housing from an initial position to the exit of the housing. In some instances, the conveyor moves the contaminated container through the interior at a constant rate. In some instances, the conveyor moves the contaminated container through the interior at a variable speed.

In some instances, the top load disinfecting device may include a light source positioned within the interior of the housing and configured to emit an electromagnetic wavelength onto the contaminated container as it moves through the interior of the housing. In some instances, a light source is positioned in proximity to the exit of the housing. In some instances, the housing comprises a recessed chamber, surface, or channel in proximity to a pathway through the interior of the housing, wherein the light source is positioned within the recessed chamber, surface, or channel. In some instances, the recessed chamber, surface, or channel entirely encircles or frames a pathway through the interior of the housing. In some instances, the light source is positioned within the recessed chamber, surface, or channel such that the light source emits an electromagnetic wavelength to one or more surfaces of a contaminated container as the container travels along the pathway, through the interior and past the recessed chamber, surface, or channel.

In a second set of example embodiments, a system for disinfecting a container may include a top load disinfecting device in accordance with an embodiment of the present invention.

In a third set of example embodiments, a method for disinfecting a container may include steps for: i) loading a stack of contaminated containers into the opening of a top load disinfecting device in accordance with an embodiment of the present invention; ii) actuating the drop plates to release a single contaminated container into the interior of the housing of the disinfecting device; iii) conveying the contaminated container from an initial position to an exit of the housing along a pathway through the interior; and iv) treating a surface of the contaminated container with an electromagnetic wavelength prior to the contaminated container advancing through the exit of the housing. In some instances, the step of "actuating the drop plates to release a single contaminated container into the interior of the housing the disinfecting device" further includes steps for rotating the set of drop plates between a storage, transfer, biasing, and release positions.

BRIEF DESCRIPTION OF THE DRAWINGS

It will be appreciated by those of ordinary skill in the art that the various drawings are for illustrative purposes only. The nature of the present invention, as well as other embodiments of the present invention, may be more clearly understood by reference to the brief and detailed descriptions of the invention, to the appended claims, and to the several drawings.

DETAILED DESCRIPTION OF THE INVENTION

Figure 1A:
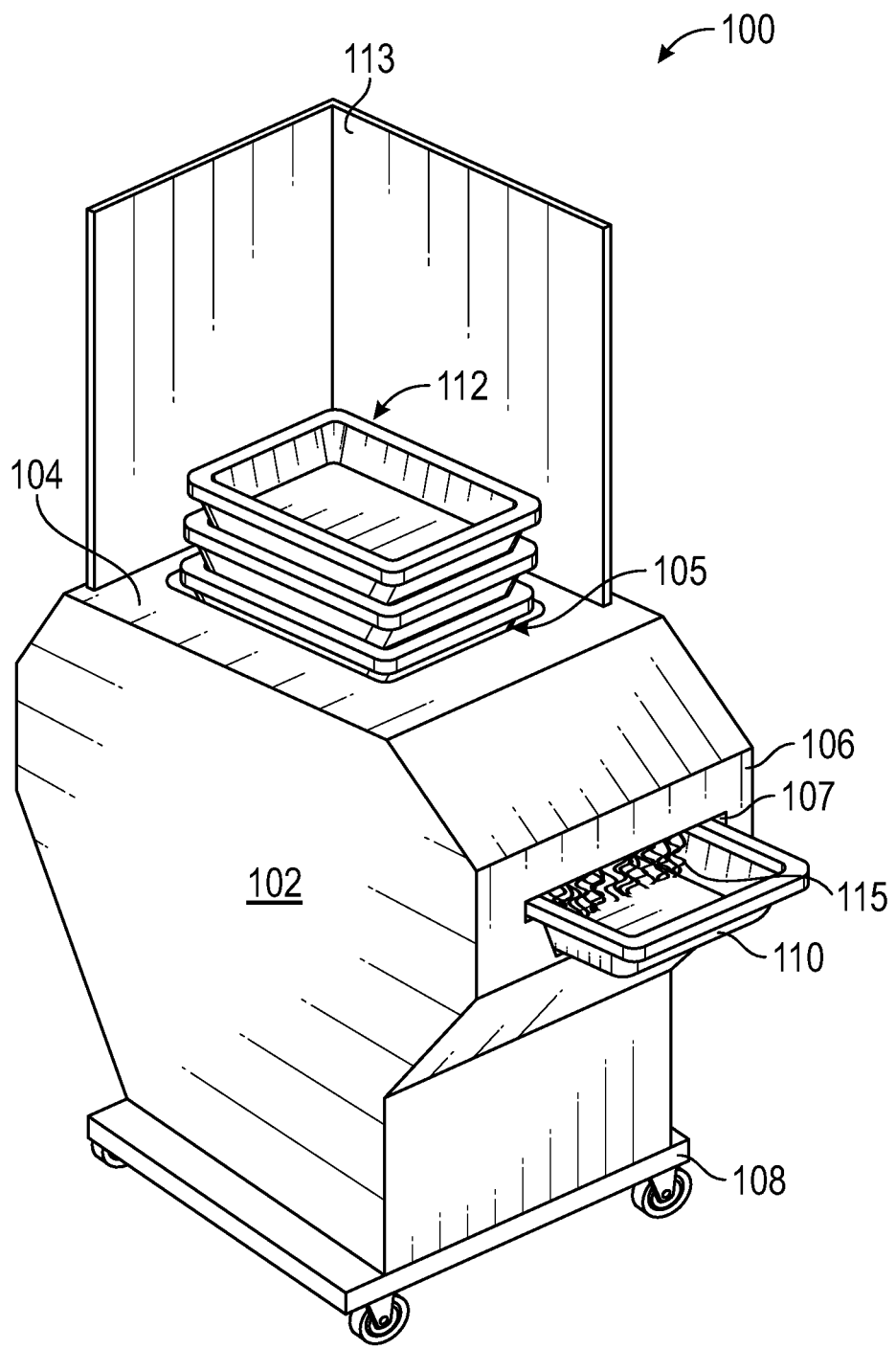
FIG. 1A is a perspective view of a top load disinfecting device in accordance with a representative embodiment of the present invention.

Referring now to FIGS. 1A-1F, a top load disinfecting device 100 is shown. In some embodiments, device 100 comprises a housing 102 generally providing an enclosure that is impervious to electromagnetic wavelengths. For example, housing 102 may include a rigid, opaque material, including but not limited to metals, a sheet metal material, such as steel, stainless steel, or aluminum, a polymer material, or a composite material. In some embodiments, the housing 102 may include a base 108 configured to stabilize the disinfecting device 100. In some embodiments, the base 108 may include wheels or another suitable mechanism to enable easy transport. In other embodiments, housing 102 is a stationary unit.

Housing 102 may include any shape, size and/or configuration compatible for use with the present invention. In some embodiments, the housing 102 may include a cube or cuboid shape. In some embodiments, the housing 102 may include at least one nonlinear surface, shape, or profile. In some embodiments, the housing 102 may include an exterior shape mirroring the interior 114 shape. In other embodiments, the housing 102 may include an exterior shape that is different than the interior 114 shape of the housing 102.

Housing 102 may include an exterior material having a first property or function, and an interior material having a second property or function that is different than the first property or function. For example, in at least one embodiment of the present invention, the housing 102 may include an exterior material that is structurally rigid and opaque, and an interior material that is reflective. In some embodiments, the interior material of the housing 102 may include a coating applied to an inner surface of the exterior material of the housing 102.

Housing 102 comprises an interior having an opening 105 located on a top surface 104 in a generally horizontal plane. Opening 105 may include a shape and/or dimensions sufficient to accommodate an outermost perimeter or periphery of the container 110. In some embodiments, the opening 105 may enable the contaminated container 110 to remain substantially level as it passes therethrough.

Opening 105 is sized and configured to receive a stack of contaminated containers 110, such that a minimal gap is provided between an outer perimeter of containers 110 and opening 105. In some embodiments, a gap between opening 105 and containers 110 is minimized to prevent leakage of emitted light therebetween. In some embodiments, individual contaminated containers 110 in a stack of contaminated containers 110 may be released through the opening 105 in succession.

Housing 102 further comprises an exit 107 forming an opening located on a distal surface 106 in a generally vertical plane. Exit 107 is sized and configured to permit passage of a disinfected container 112, such that a minimal gap is provided between an outer end cross section perimeter of container 112 and exit 107. In some embodiments, a gap between exit 107 and container 112 is minimized to prevent leakage of emitted light therebetween. In some embodiments, the exit 107 in the distal surface 106 may include a shape and dimensions to substantially match a profile or cross-section of the container 110. In some embodiments, there may be a tight tolerance between opening 105, exit 107 and the surfaces of the container 110 as the container 110 passes therethrough. In some embodiments, opening 107 further comprises a light seal 115 configured to minimize or eliminate leakage of emitted light.

In some embodiments, the top surface 104 may be substantially above the distal surface 106. In some embodiments, the top surface 104 may be aligned with the distal surface 106 or may be transverse relative to the distal surface 106. For example, in some embodiments, the housing 102 may include a cuboid, prismatic or other three-dimensional shape. In these and other embodiments, the top surface 104 may be located on an elevated surface of the housing 102 and the distal surface 106 may be located beneath the top surface 104 on a side surface or end of the housing 102.

In some embodiments, a screen 113 may be coupled to or positioned adjacent to the top surface 104 of the housing 102 to prevent undesired contact with containers 110 prior to disinfection. In some embodiments, the screen 113 may include a substantially rigid barrier having a shape to prevent access to containers 110 loaded for disinfection. For example, in some embodiments, the screen 113 may include at least one vertically oriented panel fabricated from a solid or substantially solid lightweight material such as an acrylic, plastic, or mesh. In some embodiments, the screen 113 may include a metal or plastic frame configured to support one or more panels attached thereto. In some embodiments, the panels may be removable and/or replaceable relative to the frame. In one embodiment, the screen 113 may include two vertically oriented panels positioned at right angles relative to each other to form an L-shape.

In some embodiments, the screen 113 may be positioned to surround at least a portion of the opening 105 in the top surface 104, thereby obstructing access to containers 110 prior to disinfection. In some embodiments, the screen 113 may include dimensions slightly larger than the opening 105 and a height selected to enable containers 110 to be stacked within the boundaries created by the screen 113.

Device 100 further comprises an interior 114 having dimensions sufficient to enclose a contaminated container 110. Interior 114 comprises a support surface 128 positioned below opening 105 and extending towards exit 107. Support surface 128 comprises a starting or initial position directly beneath opening 105 such that when container 110 is released into interior through opening 105, the container lands on or at the starting or initial position 103. In some embodiments, support surface 128 is a smooth surface across which container 110 may be slid from the initial position 103 to the exit 107. In some embodiments, support surface 128 may comprise an opening, a gap, or a translucent/transparent portion or material configured to permit passage of electromagnetic wavelengths emitted from a light source 136 of device 100. For example, a support surface 128 may comprise a plurality of cutouts, a wire mesh, or set of rollers having spaces through which an electromagnetic wavelength may pass.

In some embodiments, support surface 128 comprises a conveyor 130 configured to actively slide or otherwise move container 110 from the initial position 103 to the exit 107. Support surface 128 may comprise an opening or slot extending from the initial position 103 and towards exit 107, wherein the opening or slot provides a pathway through support surface 128 to permit passage of a portion of conveyor 130 to contact container 110. For example, an arm or pushing surface of conveyor 130 may extend through support surface 128 to contact a proximal end of container 110 while in the initial position 103, and convey container 110 towards and through exit 107. An arm or extension of conveyor 130 may be driven by a motor 134 and threaded rod 132 whereby the conveyor 130 moves distally and proximally between initial position 103 and exit 107 as motor 134 rotates the threaded rod 132 in clockwise and counterclockwise directs. Alternatively, conveyor 130 may be coupled to a motor 134 via a belt whereby conveyor 130 moves distally and proximally between initial position 103 and exit 103 as motor 134 turns the belt in forward and rearward directions.

In some embodiments, one or more guides 129 may be positioned within the interior 114 of the housing 102 to maintain proper orientation and prevent binding of container 110 as it is conveyed from initial position 103 to exit 107 via conveyor 130. In some embodiments, guide 129 may include an elongate panel made of metal, plastic, composite, or another suitable rigid material. In some embodiments, guide 129 comprises a channel or edge configured to receive or otherwise accommodate a lip or rim of container 110. In some embodiments, guide 129 comprises a translucent material, or may include various apertures or a mesh structure to enable light to pass through guide 129 to permit emitted light to pass through guide 129 and contact container 110.

In some embodiments, guide 129 is positioned to create a rigid boundary to prevent lateral movement of the container 110 relative to the conveyor 130. In some embodiments, one or more guides 129 extend horizontally along support surface 128 between initial position 103 and exit 107. In some embodiments, one or more guides 129 extends along a maximum travel distance of conveyor 130. In some embodiments, guides 129 are angled inwardly to provide a funneled or tapered guide towards exit 107. Guides 129 may funnel the container 110 towards and align container 110 with exit 107 as container 110 is conveyed from initial position 103 to exit 107 via conveyor 130, wherein guides 129 center and stabilize the container's position relative thereto.

Device 100 further comprises a light source 136 configured to emit an electromagnetic wavelength onto a surface of the contaminated container 110 as it moves from the initial position 103 to the exit 107. Light source 136 may include any type, shape, size, and configuration of light bulb or other form of light source compatible with a disinfecting device disclosed herein. In some instances, a light source further comprises a driver, software and other electrical components adapted to control one or more functions of the light source. In some instances, a light source of the present invention is a pulsed gas discharge lamp configured to emit a high intensity, electromagnetic wavelength. In some instances, a light source is provided configured to emit a pulsed electromagnetic wavelength. In some instances, light source 136 is a UV lamp, including, but not limited to a pulsed UV lamps, a xenon-mercury short-arc lamp, a xenon short-arc lamp, a mercury short-arc lamp, an argon arc lamp, a deuterium arc lamp, a metal-halide arc lamp, a ceramic xenon lamp, a gas-discharge lamp, a high intensity pulse lamp, a UV LED, a UV laser, a synchrotron light source, and the like.

In some embodiments, light source 136 is positioned between initial position 103 and exit 107, and in proximity to support surface 128, such that as container 110 is conveyed along support surface 128 and towards exit 107, container 110 is exposed to emitted light from light source 136. In some embodiments, light source 136 is positioned in proximity to exit 107. In some embodiments, interior 114 further comprises a recessed chamber, surface or channel in which light source 136 is housed. In some embodiments, a recessed chamber, surface or channel surrounds support surface 128 such that a light source 136 positioned therein may emit light 360° around container 110 as container 110 is conveyed past light source 136 towards exit 107. In some embodiments, a recessed position of light source 136 assists in directing emitted light onto the surfaces of container 110 and away from opening 105 and exit 107, wherein electromagnetic wavelengths from light source 136 are emitted in a direction that is perpendicular to support surface 128. In some embodiments, electromagnetic wavelengths from light source 136 are emitted in a direction that is perpendicular to a pathway along support surface 128 from initial position 103 to exit 107.

Device 100 further comprises a set of drop plates 120 arranged in proximity to opening 105. Drop plates 120 provide a dual function of supporting a stack of contaminated containers 110 within opening 105, and selectively separating and releasing the bottommost container 110 in the stack of containers, such that the bottommost container falls through opening 105 and lands on support surface 128 at the initial position 103. Drop plates 120 are configured to uniformly release the bottommost container 110 in a level, horizontal orientation such that the released container falls flat onto support surface 128 without substantial shifting, rotating or flipping of the container's orientation and position. In some embodiments, a set of drop plates 120 comprises four drop plates arranged in proximity to the corners of contaminated containers 110. In other embodiments, a set of drop plates 120 may include any number and positioning of drop plates sufficient to support a container.

Drop plates 120 may comprise upper and lower portions for supporting contaminated containers 110. Drop plates 120 are configured to rotate about a central axis of the drop plates whereby various surfaces of the drop plates facilitate separation and release of individual containers 110 into interior 114, as discussed in detail below.

Each drop plate 120 is coupled to and supported by a vertical axle 116 configured to rotate each respective drop plate 120 about a central vertical axis 118 of the axle and/or drop plate. The rotation of the set of drop plates 120 is coordinated and synchronized such that contact between each drop plate 120 and surfaces of container 110 is identical at the respective location of each drop plate 120. In some embodiments, drop plates 120 are driven by a motor 126 coupled to the drop plates 120 via vertical axles 116 operably coupled to the motor 126 via a pulley and belt, or a system of pulleys and belts. In some embodiments, a single motor 126 is used to drive all axles 116 and drop plates 120. In some embodiments, individual motors are used to drive each of the axles and drop plates independently. In some embodiments, each drop plate in a set of drop plates rotates in same direction when separating and releasing a container 110 into opening 105. In some embodiments, each drop plate in a set of drop plates rotates in a different direction when separating and releasing a container 110 into opening 105.

Disinfecting device 100 further comprises a controller unit 141 configured to control all operational components of the disinfecting device 100, including processors, motors, conveyor 130, light source 136, timers, sensors, coverings or doors for the opening 105 and exit 107, and the like. Controller unit 141 may include computer-readable software configured to control the various components of device 100. In some embodiments, the controller unit 141 may be disposed within interior 114.

Figure 1B:
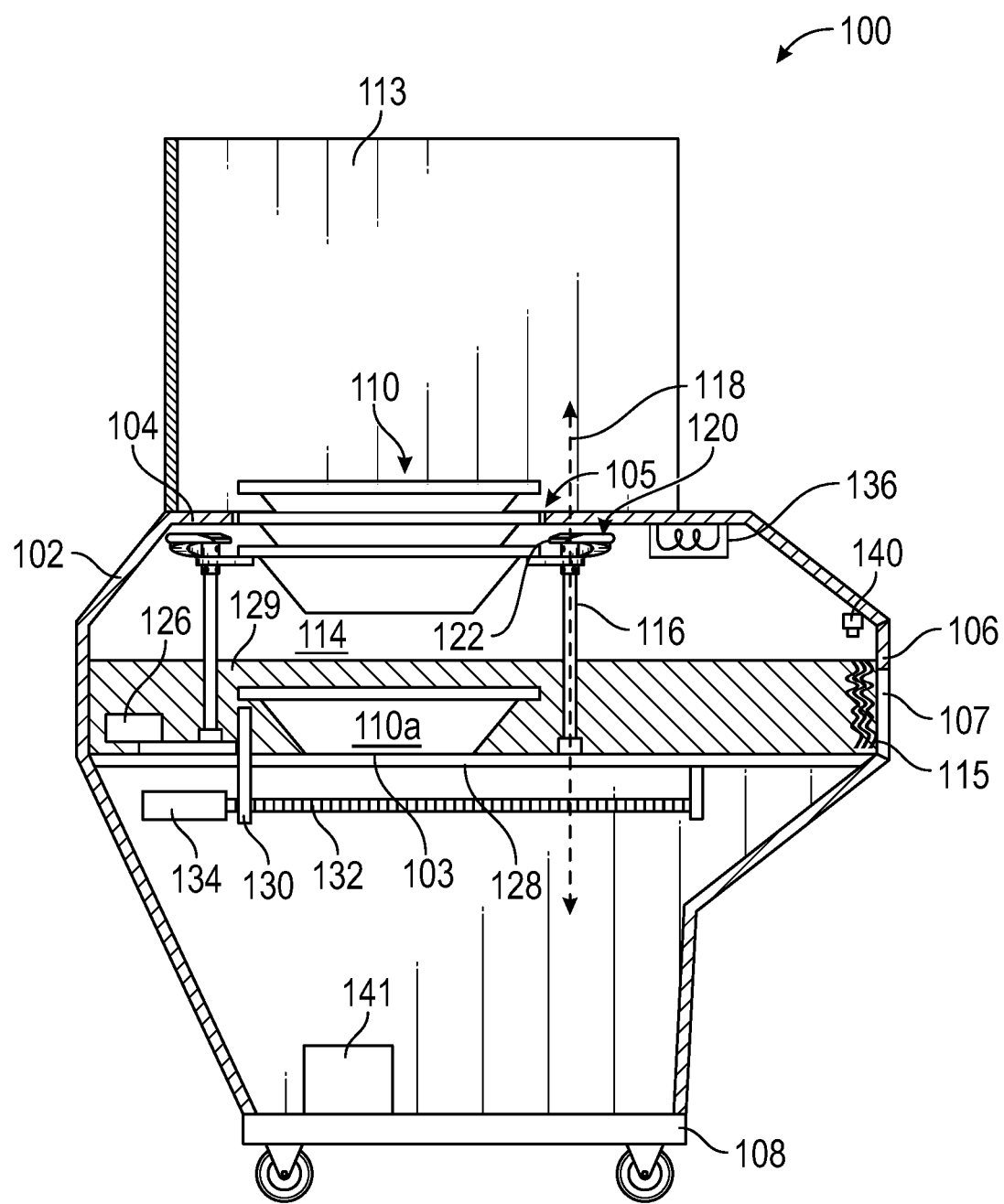
FIG. 1B is a cross-sectional side view of a disinfecting device illustrating a contaminated container disposed at an initial position within an interior of the device in accordance with a representative embodiment of the present invention.

Referring now to FIG. 1B, disinfecting device 100 is shown following the release of the bottommost contaminated container 110a from the stack of contaminated containers 110, wherein the bottommost container 110a is dropped through opening 105 onto initial position 103 of support surface 128. Prior to disinfection, conveyor 130 is in a ready position adjacent to, but not within initial position 103, such that container 110a may be dropped onto initial position 103 without contacting conveyor 130. In some embodiments, motor 134 or controller unit 141 may include a sensor to detect a ready position of conveyor 130 to prevent premature release of container 110a from stack of containers 110.

Figure 1C:
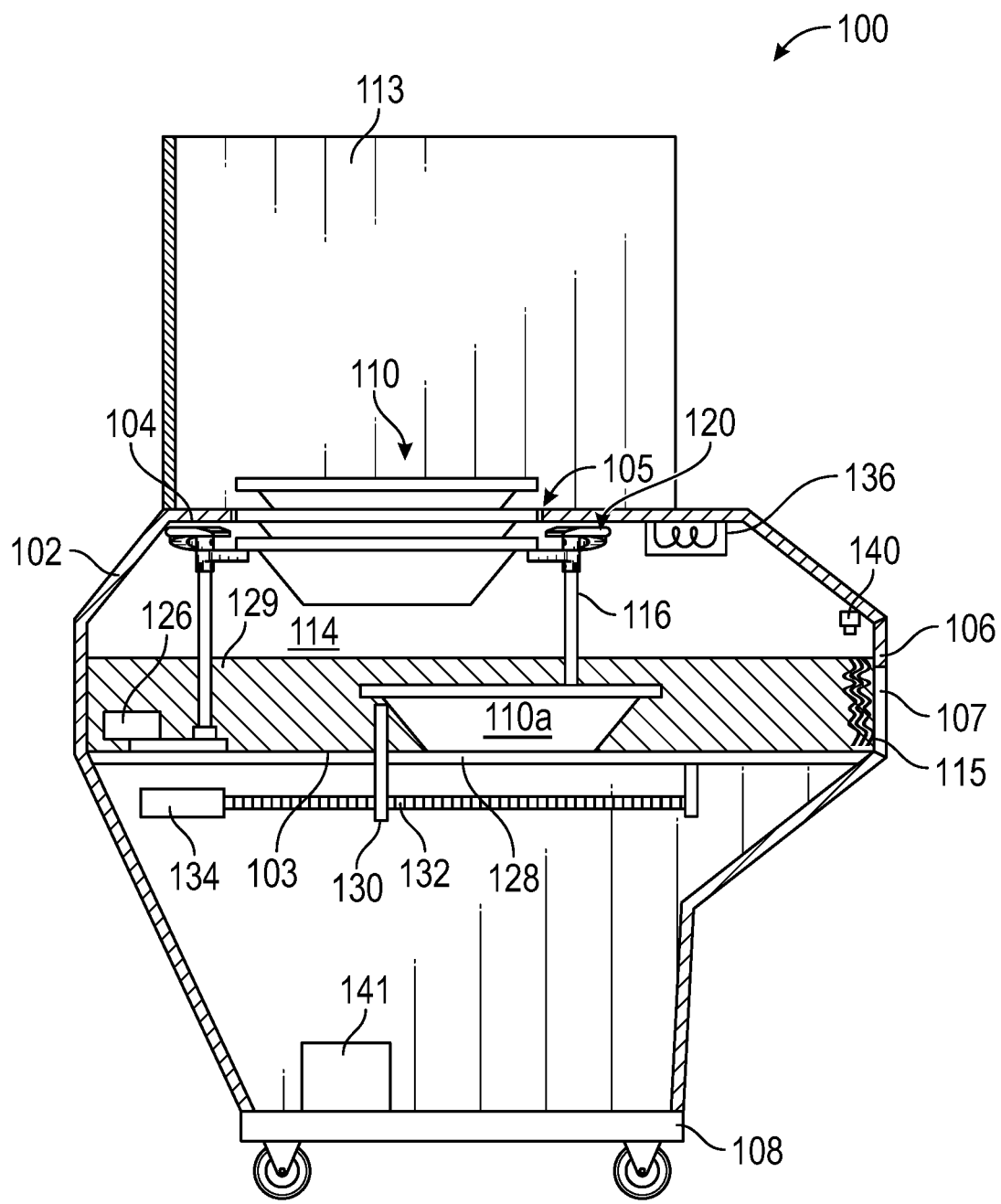
FIG. 1C is a cross-sectional side view of a disinfecting device illustrating a contaminated container being conveyed through an interior of the device via a conveyor in accordance with a representative embodiment of the present invention.

Following the release of bottommost container 110a, motor 134 is actuated to move conveyor 130 in a distal direction towards exit 107, as shown in FIG. 1C. Conveyor 130 contacts a proximal end of container 110a to advance container 110a towards exit 107. In some embodiments, conveyor 130 may comprise a shape or surface configured to compatibly contact proximal end, or some other surface of container 110a convey container 110a along support surface 128. In some embodiments, conveyor 130 may be configured to maintain a desired orientation of container 110a as container 110a is conveyed along support surface 128. Conveyor 130 may be configured to selectively connect to, connect with, engage, or otherwise temporarily retain container 110a during conveyance, wherein conveyor 130 releases container 110a following the disinfection process.

Figure 1D:
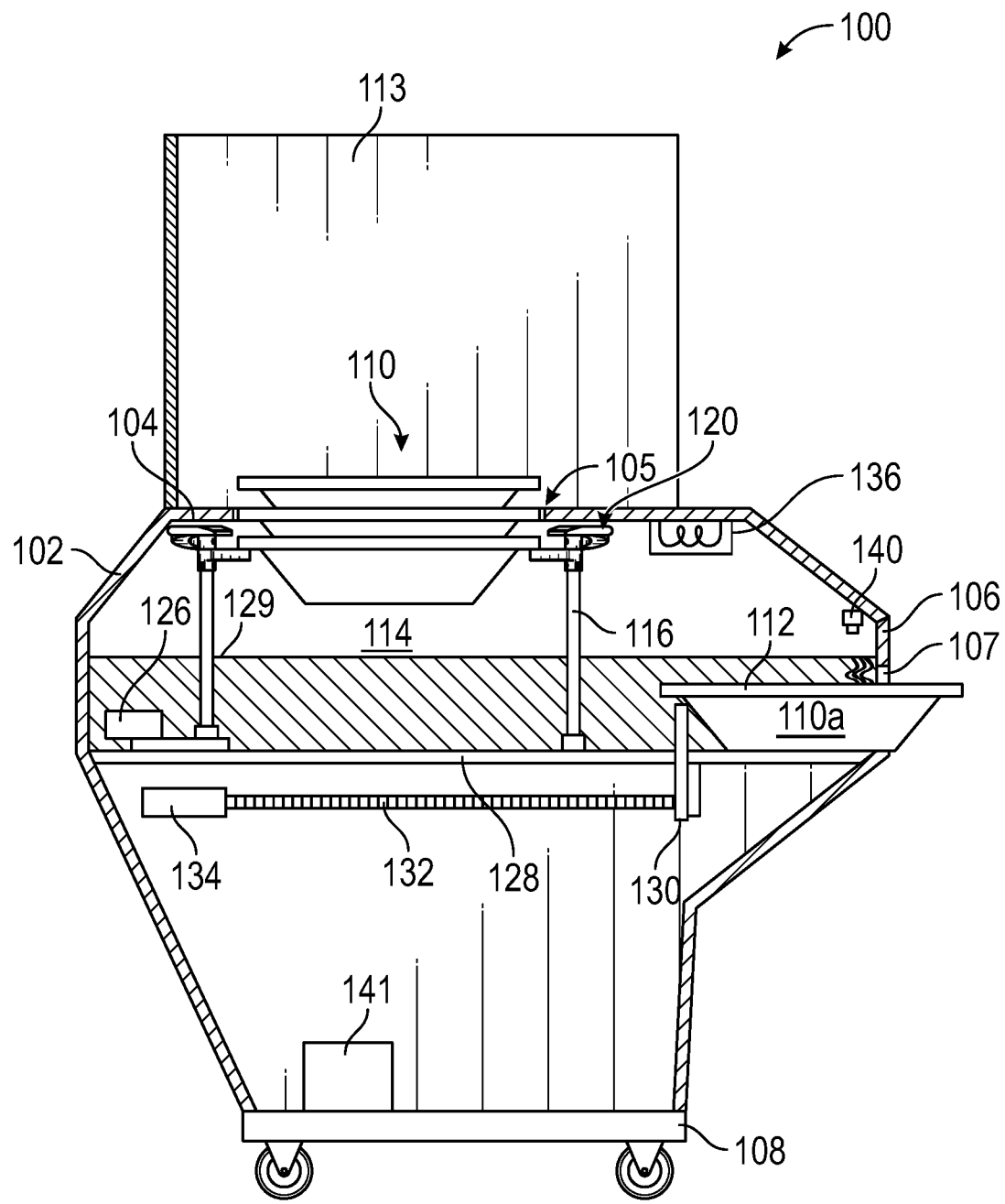
FIG. 1D is a cross-sectional side view of a disinfecting device illustrating a disinfected container positioned within an exit of the device in accordance with a representative embodiment of the present invention.
Figure 1E:
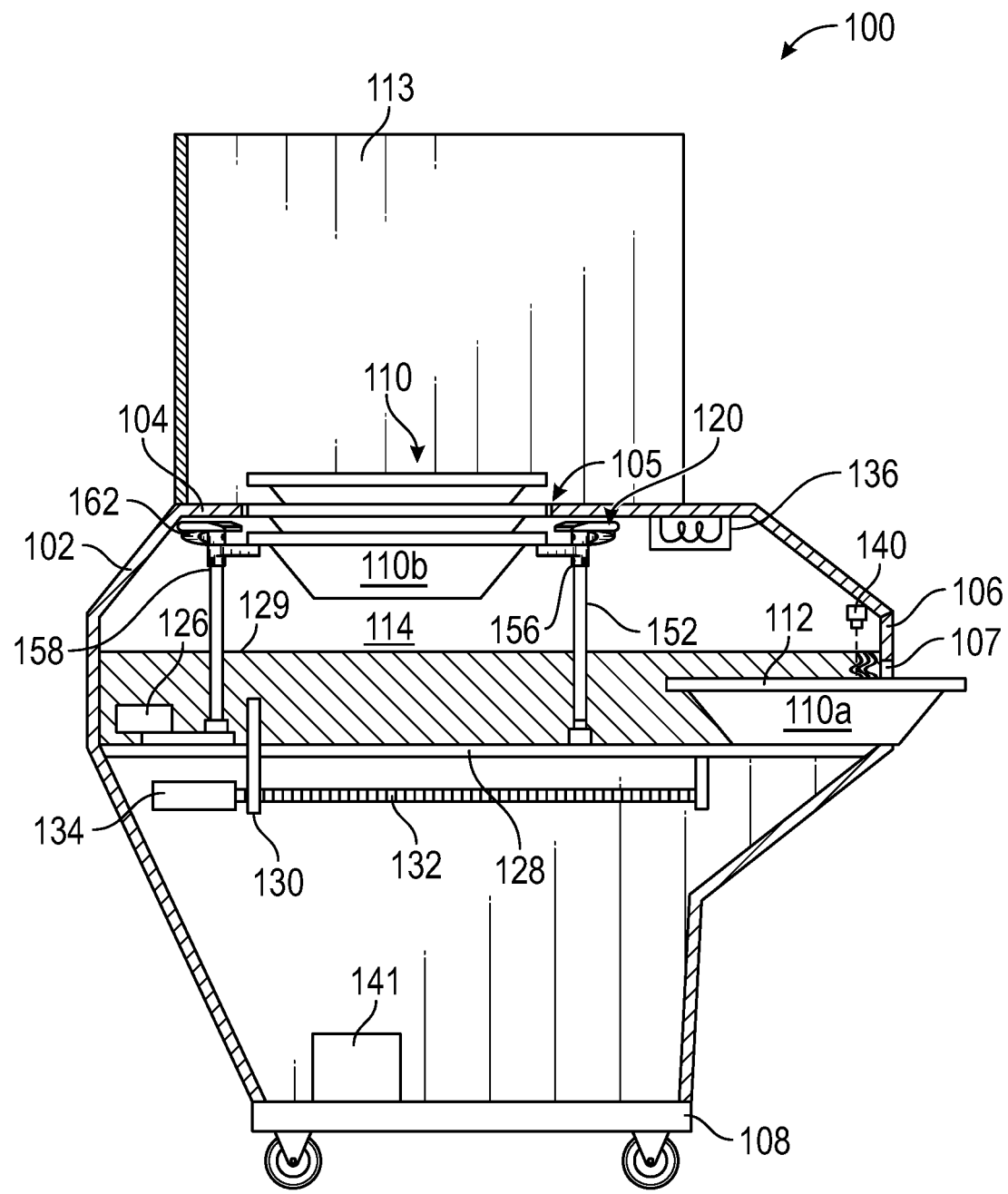
FIG. 1E is a cross-sectional side view of a disinfecting device illustrating a conveyor in a ready position in accordance with a representative embodiment of the present invention.

Referring now to FIG. 1D, container 110a is treated with electromagnetic wavelengths emitted from light source 136 as conveyor 130 conveys container 110a under, by or through light source 136. Conveyor 130 is configured to advance container 110a to a finished position whereby container 110a is located within exit 107, and a distal end of container 110a extends beyond exit 107. A sensor 140 is located in proximity to exit 107 and is configured to detect the presence of container 110a (i.e., disinfected container 112) in the finished position, whereby container 110b is separated and released from stack of container 110 until sensor 140 no longer detects container 110a in the finished position. Sensor 140 may include any compatible sensor type, including but not limited to, infrared, laser or a mechanical switch. Conveyor 130 leaves container 110a in the finished position and returns to the ready position, as shown in FIG. 1E.

In some embodiments, sensor 140 may be bypassed to enable continuous operation of the drop plates and conveyor, wherein the drop plates are actuated to release and drop container 110b as soon as conveyor 130 is returned to the ready position.

Figure 1F:
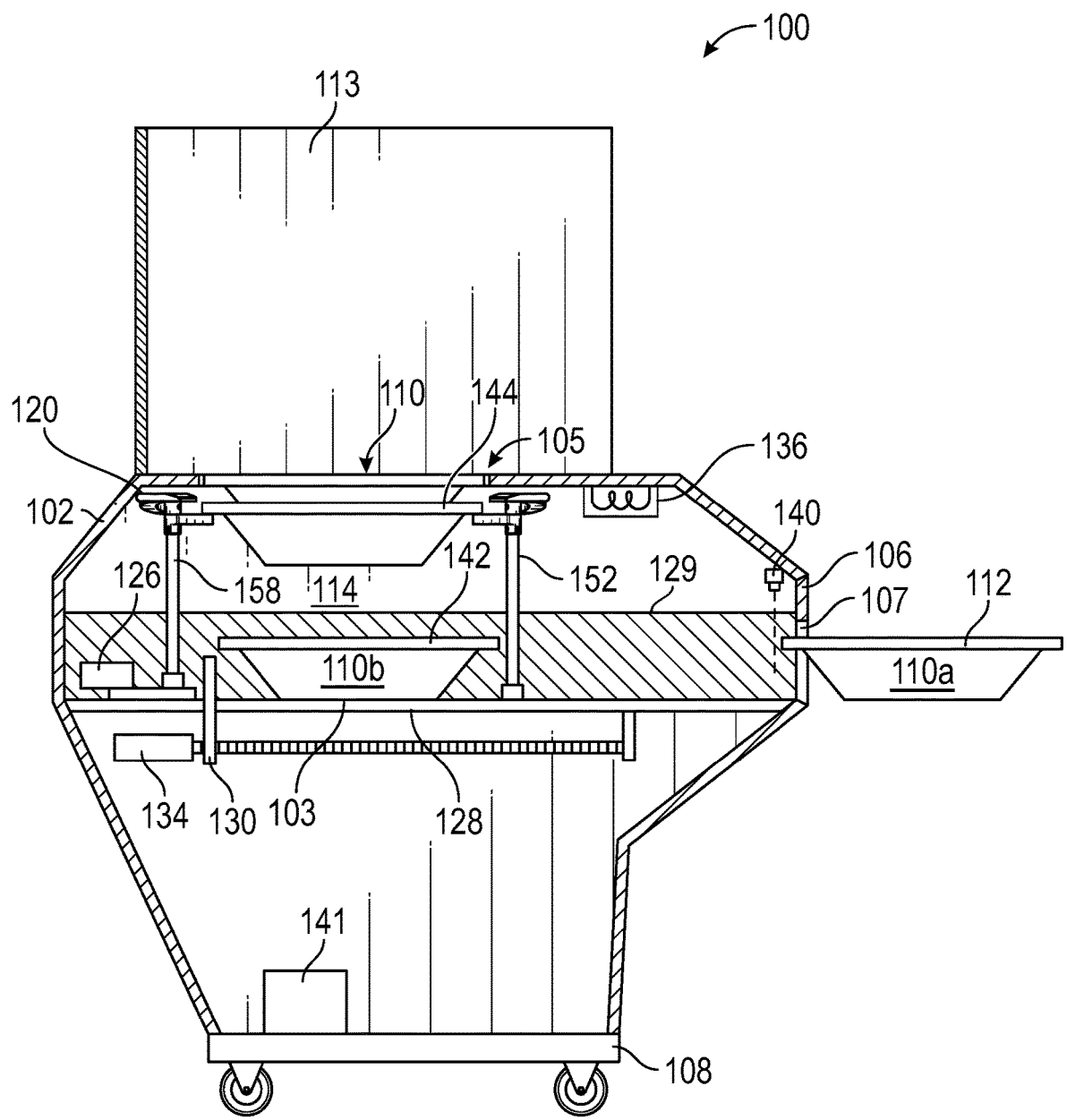
FIG. 1F is a cross-sectional side view of a disinfecting device illustrating the removal of a disinfected container from an exit of the device and the release of a second contaminated container into the initial position of the pathway through the interior of the housing of the device in accordance with a representative embodiment of the present invention.

Referring now to FIG. 1F, container 110a is shown following removal from exit 107, whereby sensor 140 no longer detects the presence of container 110a in the finished position. Upon removal of container 110a from the finished position, drop plates 120 are actuated to separate and release bottommost contaminated container 110*b* from the stack of contaminated container 110, and into the initial position 103, thereby restarting the disinfection process.

In some embodiments, controller unit 141, motor 134 and conveyor 130 may be configured to advance container 110 along support surface 128 at varied speeds depending upon the location of container 110. For example, in some embodiments container 110 is conveyed from initial position 103 to a position adjacent light source 136 at a first speed, and is further conveyed under, by or through light source 136 at a second speed, wherein the first speed is greater than the second speed. In some embodiments, the second speed is greater than the first speed. In some embodiments, the first and second speeds are the same, such that the container 110 is conveyed from the initial position 103 to the exit 107 at a constant speed. The speed of conveyance may be varied to minimize the duration of travel for container 110*a* through non-disinfecting portions of housing 102, and achieve a desire level of disinfection. For example, a speed of the conveyor 130 to convey container 110 between the initial position 103 and a position adjacent to the light source 136 may be greater than 10 ft/sec, 10 ft/sec, 9 ft/sec, 8 ft/sec, 7 ft/sec, 6 ft/sec, 5 ft/sec, 4 ft/sec, 3 ft/sec, 2 ft/sec or 1 ft/sec. In contrast, a speed of the conveyor 130 to convey container 110 under, by or through light source 136 and to the finished position may be less than 0.1 ft/sec, 0.1 ft/sec, 0.2 ft/sec, 0.3 ft/sec, 0.4 ft/sec, 0.5 ft/sec, 0.6 ft/sec, 0.7 ft/sec, 0.8 ft/sec, 0.9 ft/sec, or 1.0 ft/sec, as shown in FIG. 1D. Following the disinfection process, a speed of the conveyor 130 to return to the ready position may be greater than 10 ft/sec, 10 ft/sec, 9 ft/sec, 8 ft/sec, 7 ft/sec, 6 ft/sec, 5 ft/sec, 4 ft/sec, 3 ft/sec, 2 ft/sec or 1 ft/sec, as shown in FIGS. 1E and 1F. In some embodiments, a constant speed of the conveyor 130 to convey container from the initial position 103 to the exit 107 is greater than 10 ft/sec, 10 ft/sec, 9 ft/sec, 8 ft/sec, 7 ft/sec, 6 ft/sec, 5 ft/sec, 4 ft/sec, 3 ft/sec, 2 ft/sec, 1 ft/sec, 0.9 ft/sec, 0.8 ft/sec, 0.7 ft/sec, 0.6 ft/sec, 0.5 ft/sec, 0.4 ft/sec, 0.3 ft/sec, 0.2 ft/sec, 0.1 ft/sec, or less than 0.1 ft/sec.

Figure 2A:
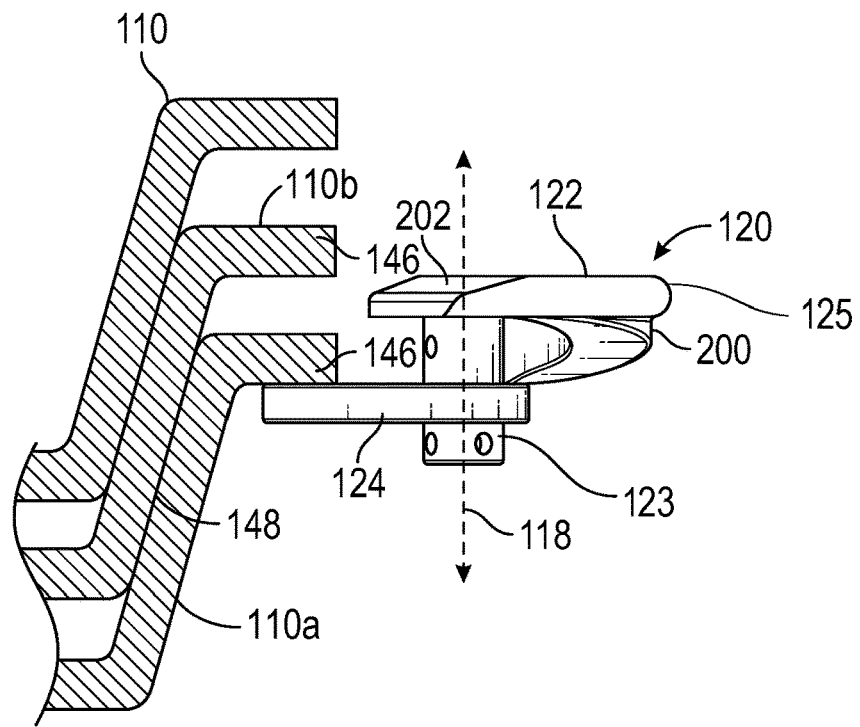
FIG. 2A is a side view of a drop plate illustrating a storage position of the drop plate whereby a stack of contaminated containers is supported on a lower portion of the drop plate in accordance with a representative embodiment of the present invention.
Figure 2B:
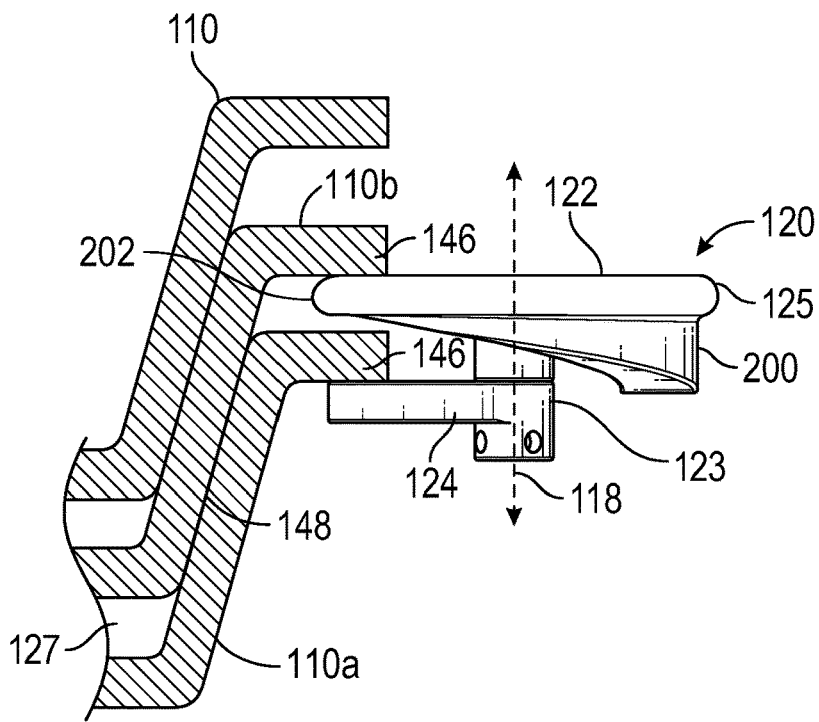
FIG. 2B is a side view of a drop plate illustrating a transfer position whereby a stack of contaminated containers is supported on an upper portion of the drop plate and the a lower contaminated container is unsupported by a lower portion of the drop plate in accordance with a representative embodiment of the present invention.
Figure 2C:
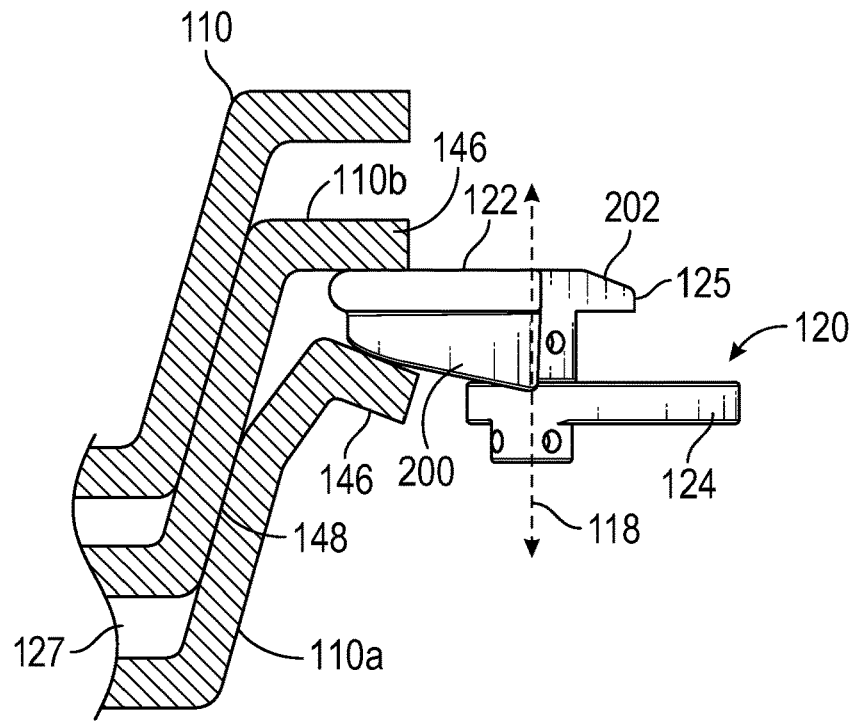
FIG. 2C is a side view a drop plate illustrating a biasing position whereby a ramped surface of the upper portion is wedged between an upper contaminated container and a lower contaminated container to bias the lower contaminated container away from the upper contaminated container in accordance with a representative embodiment of the present invention.
Figure 2D:
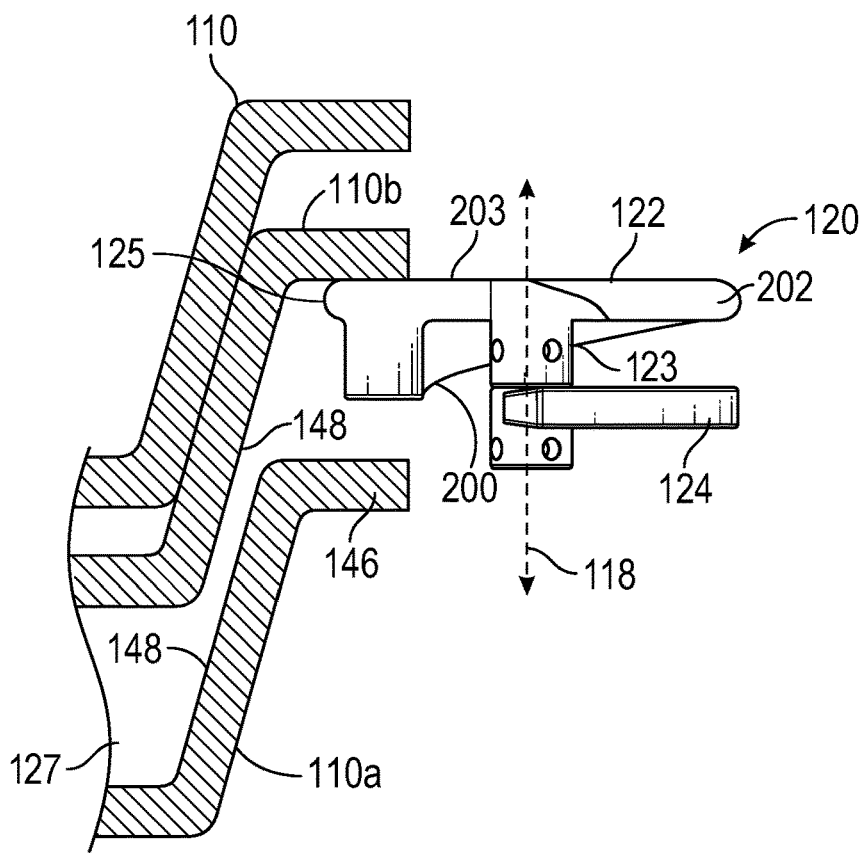
FIG. 2D is a side view of a drop plate illustrating a release position by which a ramped surface of the upper portion is fully wedged between an upper contaminated container and a lower contaminated container such that a vacuum between the lower and upper contaminated containers is broken and the lower contaminated container is released from the upper contaminated container in accordance with a representative embodiment of the present invention.
Figure 2E:
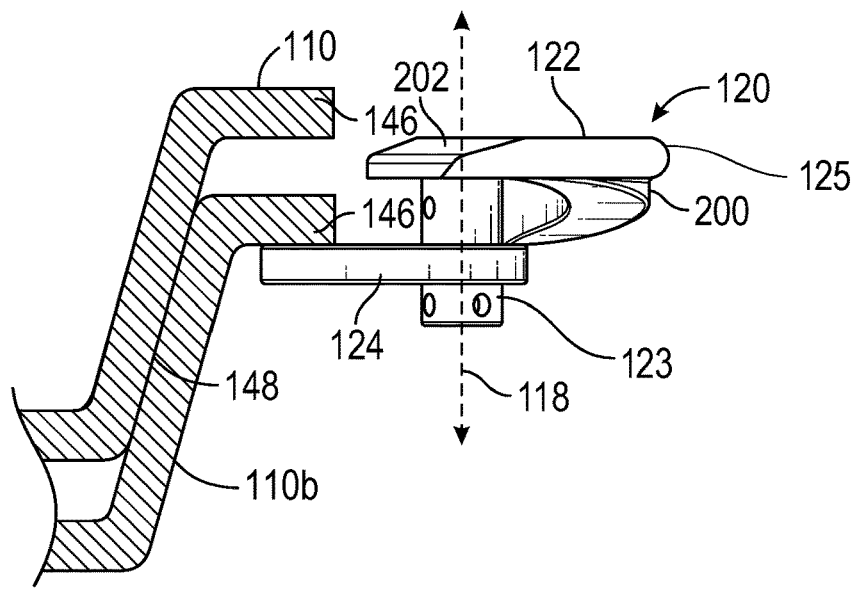
FIG. 2E is a side view of a drop plate illustrating a storage position following a release position by which a stack of contaminated containers in transferred from the upper portion to the lower portion of the drop plate in accordance with a representative embodiment of the present invention.

Referring now to FIGS. 2A-2E, a drop plate 120 and process for separating and releasing a bottommost container 110*a* from a stack of containers is shown. Drop plate 120 may include an upper portion 122 and a lower portion 124 coupled to a hub 123 and configured to support contaminated containers 110. Upper and lower portions 122, 124 are configured to interact with containers 110 when drop plate 120 is axially rotated about a central axis 118. In some embodiments, upper and lower portions 122, 124 have various surfaces designed to interact with specific surfaces of containers 110. In some embodiments, these various surfaces of upper and lower portions 122, 124 are positioned relative to one another to permit precise timing and synchronization of these surfaces with containers 110 to coordinate the separation and release a lower container 110*a* from an upper container 110*b*. In some embodiments, various surfaces of upper portion 122 are positioned out of phase, or are offset from various features of lower portion 124. In some embodiments, upper portion 122 is offset from lower portion 124 such that upper portion 122 is disengaged from containers 110 when lower plate 124 is engaged with containers 110, as shown in FIGS. 2A and 2E. Similarly, in some embodiments upper portion 122 is offset from lower portion 124 such that lower portion 124 is disengaged from containers 110 when upper plate 122 is engaged with containers 110, as shown in FIGS. 2B-2D. In some embodiments upper and lower portions 122, 124 may momentarily simultaneously engage containers 110.

In some embodiments, lower plate 124 comprises a generally planar upper surface configured to support an underside of a rim 146 of containers 110. Lower plate 124 extends outwardly from central axis 118 in a non-symmetrical orientation, such that when drop plate 120 is rotated into a storage position (i.e., FIGS. 2A and 2E), lower plate 124 is capable of supporting containers 110, however when drop plate 120 is rotated to a transfer position (i.e., FIG. 2B), a biasing position (i.e., FIG. 2C), or a release position (i.e., FIG. 2D), the lower portion is not capable of supporting containers 110. In some embodiments, lower portion 124 comprises a triangular or rectangular shape, wherein a first end of the lower portion 124 is coupled to hub 123, and wherein a second end of the lower portion 124 extends outwardly from hub 123.

In some embodiments, upper portion 122 comprises a partially rounded outer perimeter edge 125 that is at least partially offset from the second end of the lower portion 124. In the storage position, upper portion 122 is entirely disengaged from containers 110, wherein the partially rounded outer perimeter edge 125 of upper portion 122 is positioned opposite containers 110, as shown in FIG. 2A. Upper portion 122 comprises a beveled or chamfered leading edge 202 configured to assist with inserting leading edge 202 and outer perimeter edge 125 between the adjacent rims 146 of lower and upper containers 110*a*, 110*b*, as shown in FIG. 2B.

Referring now to FIG. 2B, drop plate 120 is shown in a clockwise rotated position approximately 90° from the position of drop plate 120 in FIG. 2A, wherein drop plate 120 is presently shown in a transfer position. In the transfer position, leading edge 202 and outer perimeter edge 125 are introduced into a spaced between the adjacent rims 146 of lower and upper containers 110*a*, 110*b*, and lower container 110*a* is no longer supported by lower portion 124. Accordingly, the stack of containers is transferred from lower portion 124 to upper portion 122. Although unsupported by lower portion 124, lower container 110*a* maintains its connection to upper container 110*b* via a vacuum pressure in the lumen 127 between upper and lower containers 122, 124 facilitated by a mechanical seal between sidewalls 148.

Upper portion 122 further comprises a ramped surface 200 positioned below perimeter edge 125 and tapering downward and away from leading edge 202, such that a height of the ramped surface 200 at leading edge 202 is less than a height of the ramped surface at a location spaced from leading edge 202. Ramped surface 200 is configured to contact and bias the rim 146 of lower container 110*a* downwardly and away from rim 146 of upper container 110*b*, as shown in FIG. 2C.

Referring now to FIG. 2C, drop plate 120 is shown in a clockwise rotated position approximately 90° from the position of drop plate 120 in FIG. 2B, wherein drop plate 120 is presently shown in a biasing position. In the biasing position, ramped surface 200 is wedged between rims 146 of lower and upper containers 110*a*, 110*b* to temporarily deform sidewall 148 of lower container 110*a*. Upon further clockwise rotation of drop plate 120, the mechanical seal between sidewalls 148 of lower and upper containers 110*a*, 110*b* is broken, thereby releasing the vacuum pressure from lumen 127, and releasing lower container 110*a* from upper container 110*b*, as shown in FIG. 2D.

Referring now to FIG. 2D, drop plate 120 is shown in a clockwise rotated position approximately 90° from the position of drop plate 120 in FIG. 2C, wherein drop plate 120 is presently shown in a release position. In the release position, ramped surface is fully wedged between rims 146 of lower and upper containers 110*a*, 110*b* whereby the vacuum pressure in lumen 127 is released and sidewalls 148 of lower and upper containers 110a, 110b are separated, such that lower container 110a is released from upper container 110b. Upper container 110b and the remaining container 110 in the stack of containers are supported on an upper surface 203 of upper portion 122, and lower portion 124 is positioned opposite containers 110. Following the release of lower container 110a from lower container 110b, drop plate 120 is again rotated to the storage position, as shown in FIG. 2E, and previously shown in FIG. 2A. In some embodiments, drop plate 120 rotated counterclockwise approximately 270° to return to the storage position. In other embodiments, drop plate 120 is rotated 90° clockwise to return to the storage position. In either embodiment, as drop plate 120 is rotated to the storage position, containers 110b and 110 are released from upper surface 203 of upper portion 122 and transferred to the upper surface of lower portion 124.

Figure 3A:
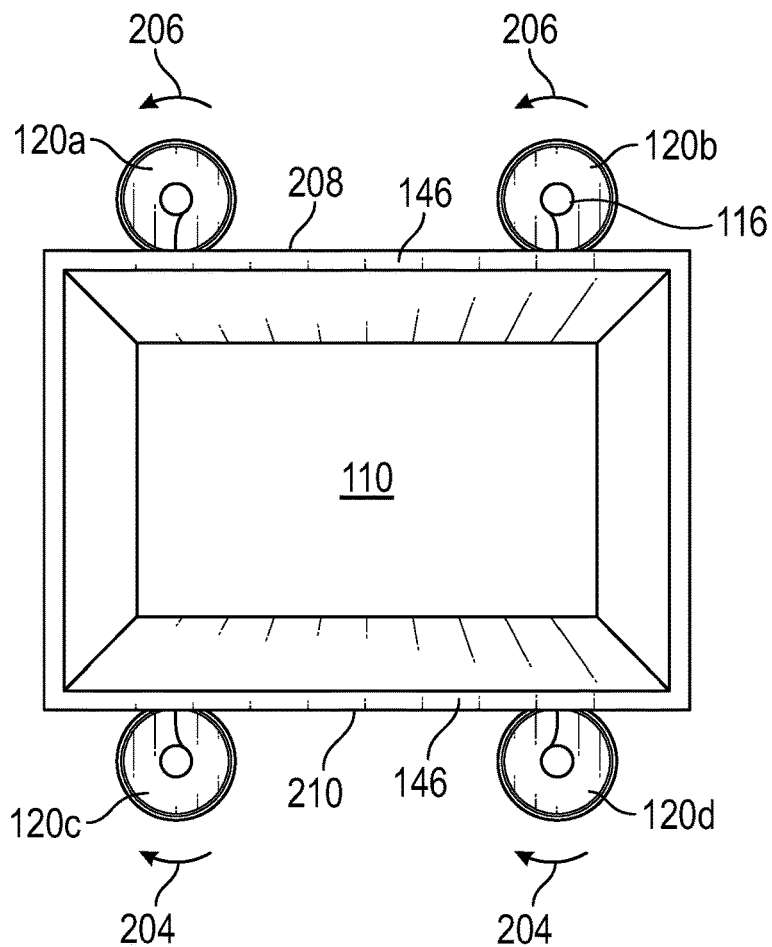
FIG. 3A is a top view of a contaminated container supported by four drop plates, and further illustrating rotation of each of the drop plates in accordance with a representative embodiment of the present invention.
Figure 3B:
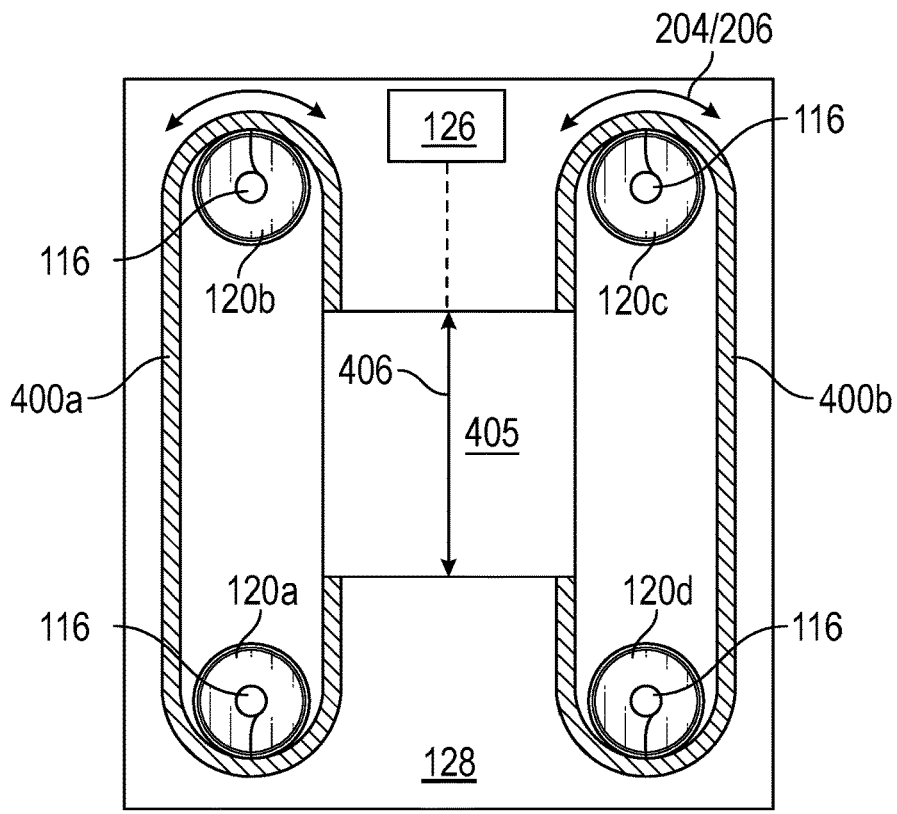
FIG. 3B is a top view of two belts driven by a single central motor and configured to coordinate and synchronize rotation of two groups of two drop plates in opposite directions of rotation in accordance with a representative embodiment of the present invention.
Figure 3C:
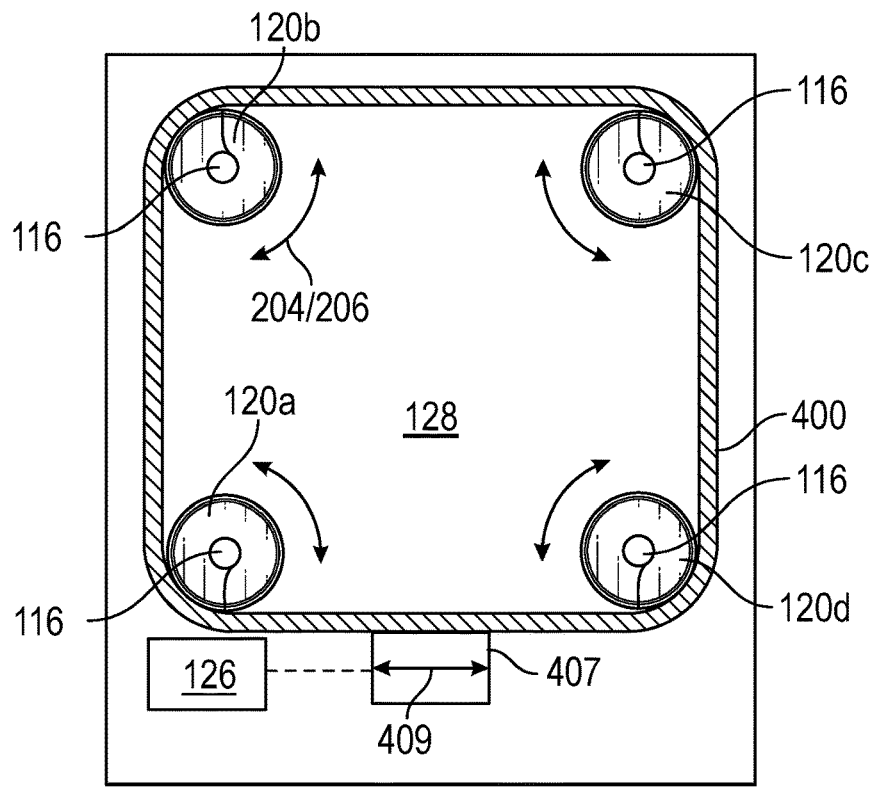
FIG. 3C is a top view of a single belt driven by a single perimeter motor and configured to coordinate and synchronize rotation of a group of four drop plates in the same direction of rotation in accordance with a representative embodiment of the present invention.

Referring generally to FIGS. 3A-3C, each drop plate 120 in a set of drop plates is coupled to and supported by a vertical axle 116 configured to rotate each respective drop plate about a central vertical axis 118 of the drop plate 120. The rotation of the set of drop plates is coordinated and synchronized such that contact between each drop plate 120 and the contaminated containers 110 is identical at the location of each drop plate 120. The vertical axles are coupled to a motor 126 that drives the rotation of the axles 116 and their respective drop plates 120. In some instances, the motor 126 is coupled to the vertical axles via a plurality of pulleys and one or more belt drives 400. In some instances, each vertical axle is directly driven by a separate motor.

Referring now to FIGS. 3A and 3B, in some embodiments a set of drop plates 120a, 120b, 120c, 120d is divided into two groups arranged on opposite sides of container 110, wherein the two groups are configured to rotate in opposite directions. For example, a first group of drop plates 120a, 120b is configured to rotate in a counterclockwise direction 206 when a second group of drop plates 120c, 120d rotates in a clockwise direction 204, as shown in FIG. 3A. As such, the surfaces and features of the drop plates 120a, 120b in the first group mirror the identical surfaces and features of the drop plates 120c, 120d in the second group.

In some embodiments, the coordinated opposite rotations of the first and second groups of drop plates is facilitated by a central drive system, wherein first and second belts 400a, 400b are coupled to a central shuttle 405 configured to move in forward and rearward directions 406, as shown in FIG. 3B. Central shuttle 405 is moved in directions 406 via a single motor 126 operably connected to central shuttle 405. In some embodiments, motor 126 is operably connected to central shuttle 405 via a belt and pulley. In other embodiments, motor 126 is operably connected to central shuttle 405 via a threaded rod assembly.

In some embodiments, a set of drop plates 120a, 120b, 120c, 120d is configured to rotate in an identical direction. As such, the surfaces and features of the drop plates 120a, 120b, 120c, 120d are identical. In some embodiments, the coordinated identical rotation of drop plates 120a, 120b, 120c, 120d is facilitated by a perimeter drive system, wherein a single belt 400 is coupled to a perimeter shuttle 407 configured to move in left and right directions 409, as shown in FIG. 3C. Perimeter shuttle 407 is moved in directions 409 via a single motor 126 operably connected to perimeter shuttle 407. In some embodiments, motor 126 is operably connected to perimeter shuttle 407 via a belt and pulley. In other embodiments, motor 126 is operably connected to perimeter shuttle 407 via a threaded rod assembly.

Figure 4A:
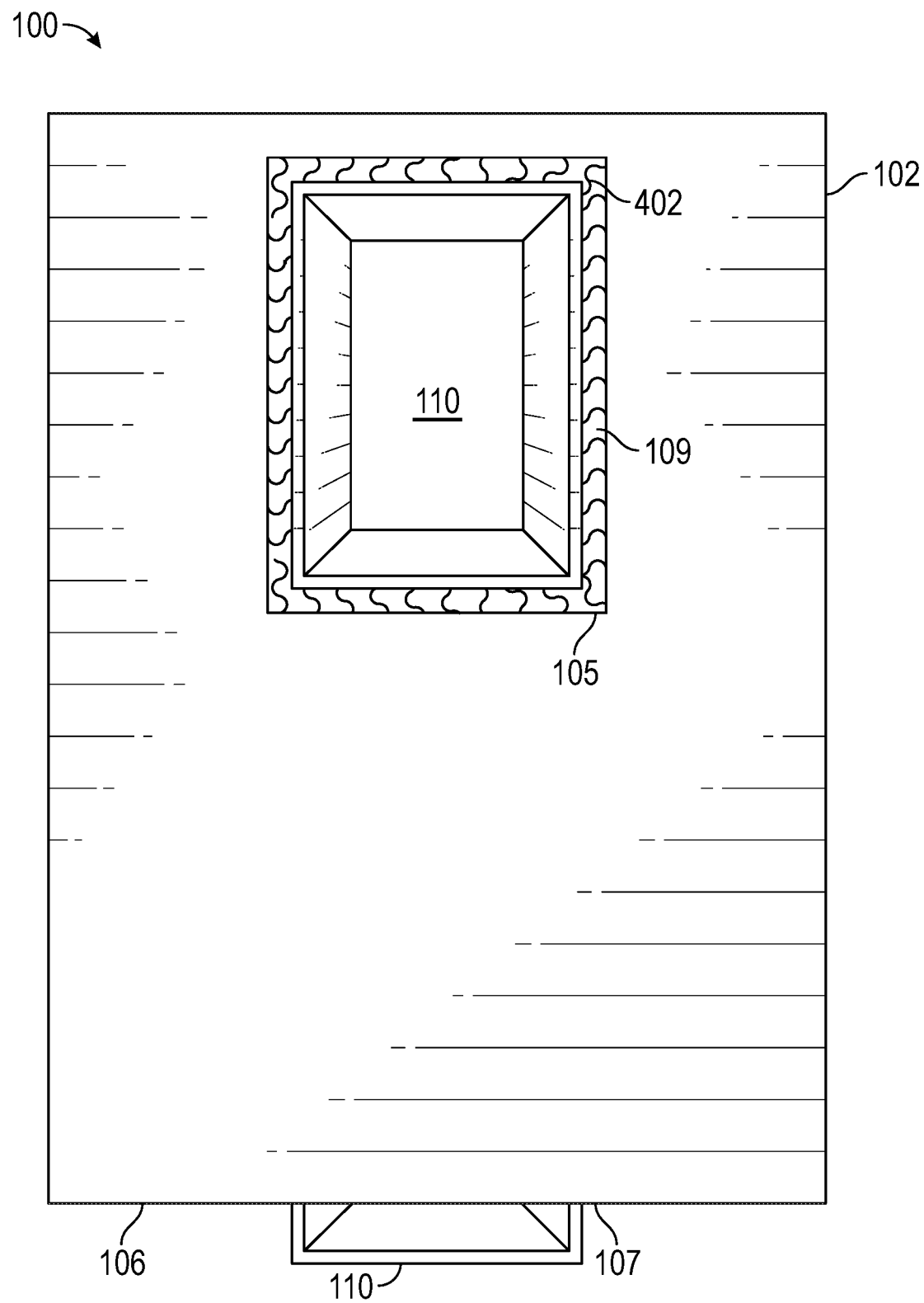
FIG. 4A is a top view of a disinfecting device having a horizontal light seal to close a gap between an opening of the device and an outer perimeter of a contaminated container positioned within the opening whereby the light seal prevents leakage of emitted light through the gap in accordance with a representative embodiment of the present invention.
Figure 4B:
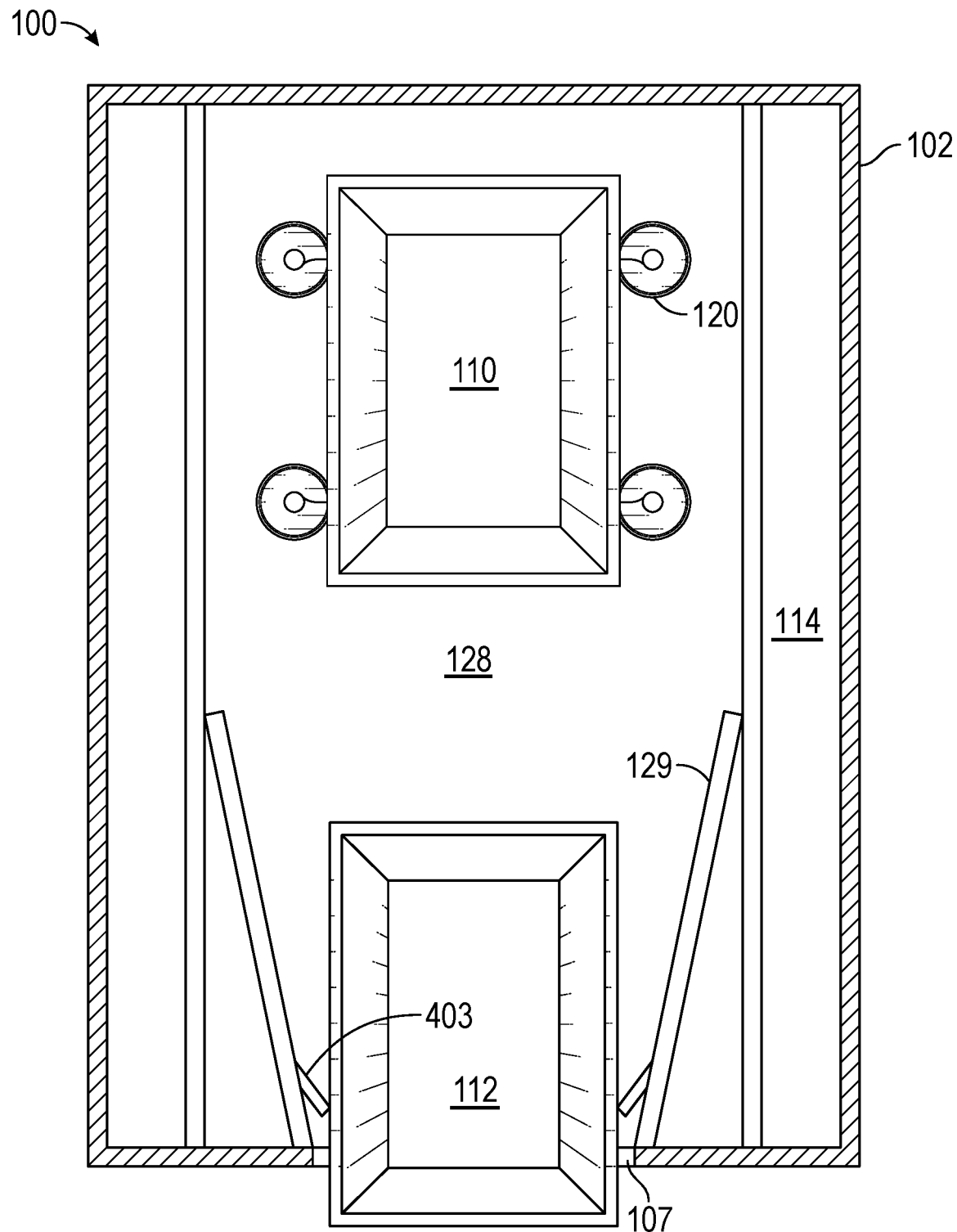
FIG. 4B is a cross-sectional top view of a disinfecting device having lateral light seals to close a gap between an exit of the device and a side surface of a container positioned within the exit whereby the lateral light seal prevents leakage of emitted light through the gap in accordance with a representative embodiment of the present invention.
Figure 4C:
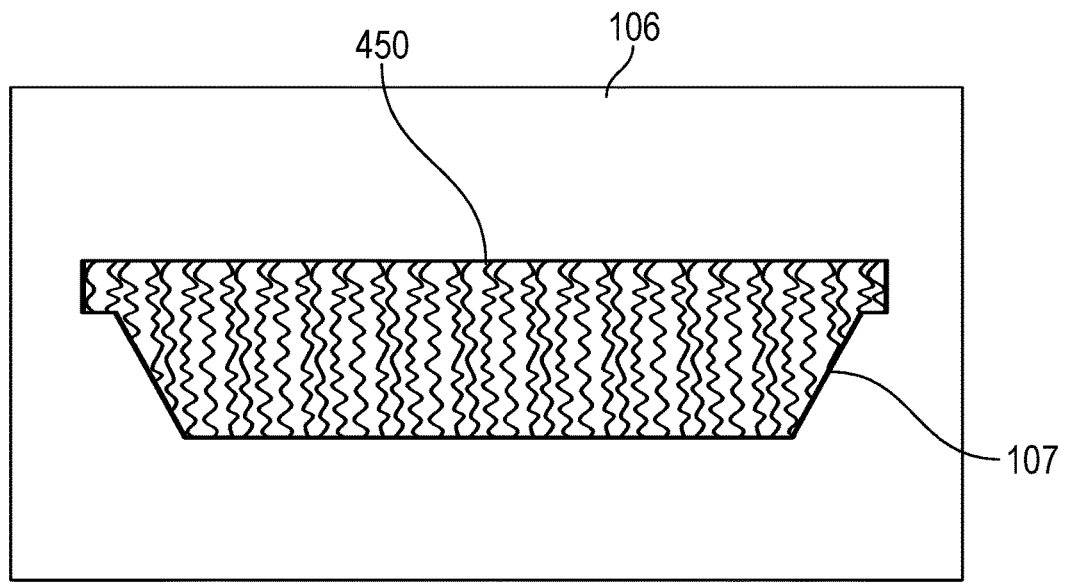
FIG. 4C is a distal end view of a disinfecting device having a vertical light seal configured to prevent leakage of emitted light through the exit of the device in accordance with a representative embodiment of the present invention.

Referring now to FIGS. 4A-4C, disinfecting device 100 may include various light seals or other structures to prevent leakage of electromagnetic wavelengths from housing 102. In some embodiments, device 100 comprises a rigid, resilient or flexible light seal configured to block harmful electromagnetic wavelengths emitted from light source 136. In some embodiments, the light seal is moved between closed and open positions by a mechanical device which may include, for example, at least one of a motor, a hinge, a driver, a sensor, a bearing, a chassis, a pivot, a driveshaft, suspension, an actuator, and/or the like. In some embodiments, the light seal may comprise a plurality of plastic strips or flexible bristles forming a brush seal that is impervious or substantially impervious to electromagnetic wavelengths. In some embodiments, a light seal is provided which may be temporarily displaced by container 110.

For example, in some embodiments a horizontal light seal 402 is positioned in opening 105 to minimize or entirely fill a gap 109 between an outer perimeter edge of container 110 and opening 105, as shown in FIG. 4A. As such, electromagnetic wavelengths are substantially or entirely prevented from leaking through gap 109. In some embodiments, lateral light seals 403 are positioned within interior 114 of housing 102 and in proximity to exit 107, wherein lateral light seals 403 are configured to minimize or entirely fill a gap between an outer sidewall surface of container 112 and exit 107, and/or a gap between an outer sidewall surface of container 112 and guides 129 at a location in proximity to exit 107, as shown in FIG. 4B. In some embodiments, lateral light seals 403 are shaped or arranged to mirror the sidewall structure of container 112. In some embodiments, lateral light seals 403 are angled distally towards exit 107, such that container 112 is prevented from binding on or deforming lateral light seals 403 as container 112 passes therethrough. In some embodiments, a vertical light shield 450 is positioned in exit 107 to entirely block electromagnetic wavelengths from leaking out of exit 107, as shown in FIG. 4C. Vertical light shield 450 is configured to be temporarily displaced by container 112 as container 112 advances through exit 107. In some embodiments, vertical light shield 450 drapes around and into container 112 when container 112 is positioned in exit 107 following a disinfection process.

Figure 5:
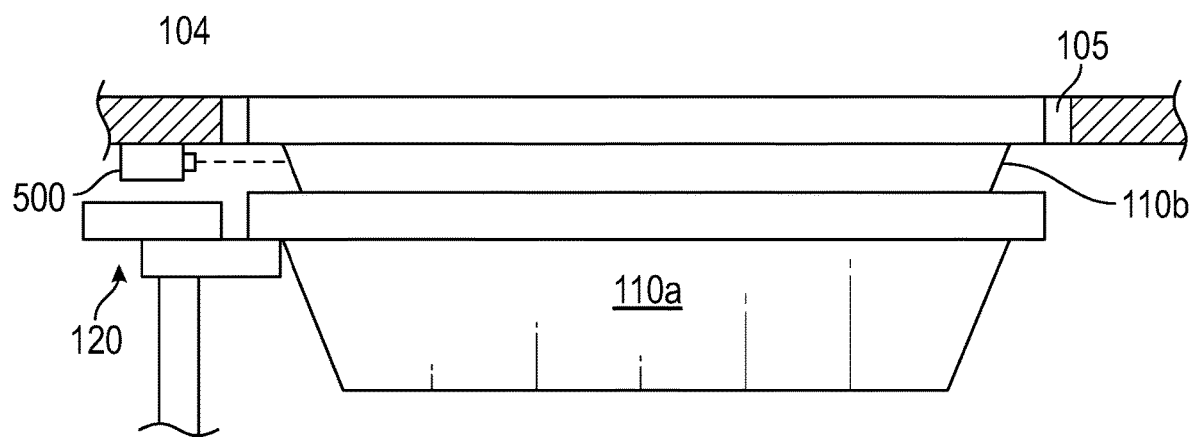
FIG. 5 is a detailed cross-sectional side view of a disinfecting device having a sensor for detecting the presence of a container within the opening in accordance with a representative embodiment of the present invention.

Referring now to FIG. 5, housing 102 may further include a sensor 500 positioned in proximity to opening 105 and configured to detect the presence of a stack of at least two containers 110 in opening 105. Sensor 500 may include any sensor described herein, or any other compatible sensor type. Sensor 500 is provided to ensure that at least one container 110b is present within opening 105 before permitting light source 136 to emit electromagnetic wavelengths. The presence of container 110b in opening 105 acts to substantially block leakage of electromagnetic wavelengths through opening 105. Thus, when a stack of two or more containers 110a, 110b is positioned within opening 105, light source 136 may be safely activated without risk of light leakage through opening 105 due to upper container 110b being positioned within opening 105. However, when lower container 110a is released, upper container 110b will be transferred to drop plate 120 and therefore will no longer be positioned within opening 105. In this configuration, sensor 500 fails to detect a stack of at least two containers, and therefore released container 110a will remain in the initial position until additional containers are added to container 110b. Upon stacking additional containers into container 110b, sensor detects a stack of at least two containers, thereby permitting the disinfection process of released container 110a to proceed. In some embodiments, sensor 500 is integrated directly into opening 105. In some embodiments, sensor 500 may be required to detect a stack of two or more containers over a predetermined time period in order to prevent false detections. In some embodiments, sensor 500 may be overridden by a user waving their hand or a similar object through the beam of sensor 500, or otherwise triggering sensor 500.

The present invention further comprises a method for disinfecting a container including steps for: i) loading a stack of contaminated containers into the opening of a top load disinfecting device in accordance with an embodiment of the present invention; ii) actuating the drop plates to release a single contaminated container into the interior of the housing of the disinfecting device; iii) conveying the contaminated container from an initial position to an exit of the housing along a pathway through the interior; and iv) treating a surface of the contaminated container with an electromagnetic wavelength prior to the contaminated container advancing through the exit of the housing. In some embodiments, the step of "actuating the drop plates to release a single contaminated container into the interior of the housing the disinfecting device" further includes steps for rotating the set of drop plates between a storage, transfer, biasing, and release positions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description.

What is claimed is:

1. A top load disinfecting device for disinfecting a container, comprising:
    a housing having a top surface comprising an opening, a distal surface perpendicular to the top surface and comprising an exit, and an interior interposed therebetween;
    a drop plate positioned in proximity to the opening and configured to support a stack of containers within the opening, and further configured to rotate in a plane parallel to the opening to selectively release a single container from the stack of containers into the interior of the housing;
    a conveyor configured to convey a container through the interior from an initial position in proximity to the opening to the exit along a pathway through the interior; and
    a light source located within the interior at a position between the opening and the exit, wherein the light source is configured to emit an electromagnetic wavelength onto a container as it passes through the interior.

2. The top load disinfecting device of claim 1, wherein the drop plate comprises an upper portion and a lower portion, wherein the upper portion extends in an opposite direction relative to the lower portion.

3. The top load disinfecting device of claim 2, wherein the lower portion and the upper portion have a fixed relationship relative to each other such that the lower portion and the upper portion rotate together about a vertical axis of drop plate.

4. The top load disinfecting device of claim 2, wherein the upper portion comprises a ramped surface configured for insertion between opposing surfaces of two adjacent containers in a stack of containers, whereby the ramped surface separates a lower container from an upper container in the stack of containers.

5. The top load disinfecting device of claim 2, wherein the drop plate is configured to rotate between a storage position, a transfer position, a biasing position, and a release position, wherein
    in the storage position a stack of containers is supported on the lower portion;
    in the transfer position a stack of container is supported on an upper surface of the upper portion, except for a bottommost container in the stack of containers which is unsupported by the drop plate;
    in the biasing position a ramped surface of the upper portion is inserted between opposing surfaces of the bottommost container and an adjacent container in the stack of containers; and
    in the release position the ramped surface of the upper portion is substantially inserted between the opposing surfaces of the bottommost container and the adjacent container in the stack of containers such that the bottommost container is separated from the adjacent container in the stack of containers and released into the initial position.

6. The top load disinfecting device of claim 5, wherein the bottommost container is released from the adjacent container in a level plane.

7. The top load disinfecting device of claim 1, wherein the drop plate comprises a plurality of drop plates arranged to support at least two corners of a stack of containers positioned within the opening.

8. The top load disinfecting device of claim 1, wherein the opening comprises a plurality of corners, each corner comprising a drop plate positioned in proximity thereto.

9. The top load disinfecting device of claim 8, further comprising a plurality of axles coupled to the plurality of drop plates, and further comprising a motor operably coupled to the plurality drop plates via the plurality of axles, wherein the motor is configured to rotate the axles about a central axis.

10. The top load disinfecting device of claim 1, further comprising a sensor configured to detect a stack of containers positioned in the opening.

11. The top load disinfecting device of claim 1, wherein the conveyor moves the container from the initial position to a position adjacent the light source at a first speed, and moves the container from the position adjacent the light source to the exit at a second speed, wherein the first speed is greater than the second speed.

12. A method for disinfecting a container, comprising:
    loading a stack of contaminated containers into an opening of a top load disinfecting device, the top load disinfecting device comprising a housing and a drop plate, wherein the drop plate is positioned in proximity to the opening and configured to support the stack of containers within the opening, and is further configured to rotate in a plane parallel to the opening to selectively release a single container from the stack of containers into an interior of the housing;
    actuating the drop plate to release a single contaminated container into the interior of the housing;
    conveying the contaminated container from an initial position to an exit of the housing along a pathway through the interior; and
    treating a surface of the contaminated container with an electromagnetic wavelength prior to the contaminated container advancing through the exit of the housing.

13. The method of claim 12, wherein the step of actuating the drop plate further comprises rotating the drop plate between a storage position, a transfer position, a biasing position, and a release position, wherein
- in the storage position a stack of containers is supported on a lower portion;
- in the transfer position the stack of containers is supported on an upper surface of an upper portion, except for a bottommost container in the stack of containers which is unsupported by the drop plate;
- in the biasing position a ramped surface of the upper portion is inserted between opposing surfaces of the bottommost container and an adjacent container in the stack of containers; and
- in the release position the ramped surface of the upper portion is substantially inserted between the opposing surfaces of the bottommost container and the adjacent container in the stack of containers such that the bottommost container is separated from the adjacent container in the stack of containers and released into the initial position.

14. The method of claim 12, further comprising a step for detecting the presence of a container within the opening prior to the step of treating a surface of the contaminated container with an electromagnetic wavelength.

15. The method of claim 12, further comprising a step for varying a speed of the contaminated container along the pathway through the interior.

\* \* \* \* \*